US012799060B2

(12) United States Patent
Tsanaktsidis et al.

(10) Patent No.: US 12,799,060 B2
(45) Date of Patent: Nov. 17, 2026

(54) PURIFICATION PROCESS

(71) Applicant: COMMONWEALTH SCIENTIFIC AND INDUSTRIAL RESEARCH ORGANISATION, Acton (AU)

(72) Inventors: John Tsanaktsidis, Acton (AU); Cecily Eldridge, Acton (AU)

(73) Assignee: COMMONWEALTH SCIENTIFIC AND INDUSTRIAL RESEARCH ORGANISATION, Acton (AU)

( * ) Notice: Subject to any disclaimer, the term of this patent is extended or adjusted under 35 U.S.C. 154(b) by 499 days.

(21) Appl. No.: 18/571,528

(22) PCT Filed: Jun. 17, 2022

(86) PCT No.: PCT/AU2022/050617
§ 371 (c)(1),
(2) Date: Dec. 18, 2023

(87) PCT Pub. No.: WO2022/261728
PCT Pub. Date: Dec. 22, 2022

(65) Prior Publication Data

US 2024/0286986 A1 Aug. 29, 2024

(30) Foreign Application Priority Data

Jun. 18, 2021 (AU) ................................ 2021901845

(51) Int. Cl.
*C07C 41/42* (2006.01)

(52) U.S. Cl.
CPC .................................... *C07C 41/42* (2013.01)

(58) Field of Classification Search
CPC ......... C07C 41/42; C07C 41/46; C07C 41/38; C07C 41/01; C07C 42/12; C07C 43/137
See application file for complete search history.

(56) References Cited

FOREIGN PATENT DOCUMENTS

| | | | |
|---|---|---|---|
| CN | 105801335 | A | 7/2016 |
| GB | 523449 | A | 7/1940 |
| GB | 928786 | A | 6/1963 |
| WO | WO-2021/119716 | A1 | 6/2021 |

OTHER PUBLICATIONS

Dayan AD "Analgesic use of inhaled methoxyflurane : Evaluation of its potential nephrotoxicity", Human and Experimental Toxicology., vol. 35, No. 1, pp. 91-100, DOI: 10.1177/0960327115578743 (Apr. 28, 2015) (10 pages).
Englund, B., "2-Chloro-1,1,2-trifluoroethyl ethyl ether." Organic Syntheses. 34:16-18 (1954) (4 pages).
Ismagilov et al., "Reactions of Fluoro Monomers. I. Mechanism of the Base-Catalyzed Reaction of 1,1-dichloro-2,2-difluoroethylene with Methanol." Russian Journal of General Chemistry. 63(1, Part 2): 146-150 (1993) (5 pages).
Park et al., "Physical Properties of Some 1, 1-Difluoro-2, 2-dichloroethyl Alkyl Ethers1,2." Journal of the American Chemical Society. 73(2): 861-862 (Feb. 1951) (2 pages).
Park et al., "Polyfluoro Alkyl Ethers and their Preparation." Journal of the American Chemical Society. 70(4): 1550-1552 (Apr. 1948) (3 pages).
Sazonov et al., "A new mechanism of nucleophilic vinylic substitution and unexpected products in the reaction of chlorotrifluoroethylene with [Re(CO)5]Na and [CpFe(CO)2]K." Journal of Organometallic Chemistry. 691(11): 2346-2357 (Feb. 2006) (12 pages).
Tarrant et al., "The Addition of Alcohols to Some 1,1-Difluoroethylenes." Journal of the American Chemical Society. 73(4): 1781-1783 (Apr. 1951) (3 pages).
Troilo, G. "Chlorofluoropropane derivatives." Annali di Chimica—Rome, Italy. 58(1): 25-31 (1968) (9 pages).
Product information of "Penthrox 99.9%, 3 ml inhalation vapour, liquid." <URL:https://www.medicines.org.uk/emc/product/1939/smpc#gref> . Published on May 1, 2020. Retrieved from internet on Aug. 4, 2022 (11 pages).

*Primary Examiner* — Jafar F Parsa
(74) *Attorney, Agent, or Firm* — Clark & Elbing LLP

(57) ABSTRACT

A process for purifying halogenated alkoxyethane of general formula XClHC—$CF_2$OR, where X is —Cl or —F and OR is $C_{1-4}$ alkoxy, from a reaction mixture derived from a batch synthetic procedure for producing the halogenated alkoxyethane, the process comprising the steps of: (a) adding one of an amine and an acid to the reaction mixture, (b) adding a polar liquid to the mixture obtained in step a) to induce phase separation and formation of a polar phase and a separate organic phase, the organic phase containing the halogenated alkoxyethane, and (c) adding the other of the amine and the acid not used step (a) to the organic phase obtained in step (b) to thereby purify the halogenated alkoxyethane.

17 Claims, 2 Drawing Sheets

PURIFICATION PROCESS

FIELD OF THE INVENTION

The present invention relates in general to processes for purifying halogenated alkoxyethane, and in particular to a process for purifying halogenated alkoxyethane of general formula XClHC—$CF_2$OR, where X is —Cl or —F and OR is $C_{1-4}$ alkoxy.

BACKGROUND

Halogenated alkoxyethane compounds constitute a significant fraction of present day active pharmaceutical ingredients, not to mention agrochemicals, dyes, flame-retardants, and imaging agents.

The use of halogenated alkoxyethane compounds for use as active pharmaceutical ingredients requires the consistent provision of pharmaceutical grade halogenated alkoxyethane. Conventionally, halogenated alkoxyethane is produced in batch synthetic procedures. However, those procedures struggle to afford direct production of high purity halogenated alkoxyethane and must be complemented by post-production purification procedures. Those purification procedures are mostly based on physical removal of impurities and are inherently plagued by low efficiencies and high operational costs.

Accordingly, there remains an opportunity to provide purification procedures of halogenated alkoxyethane that can complement conventional batch synthesis of halogenated alkoxyethane and be effective to provide pharmaceutical grade compound at a commercially relevant scale.

SUMMARY OF THE INVENTION

The present invention provides a process for purifying halogenated alkoxyethane of general formula XClHC—$CF_2$OR, where X is —Cl or —F and OR is $C_{1-4}$ alkoxy, from a reaction mixture derived from a batch synthetic procedure for producing the halogenated alkoxyethane, the process comprising the steps of:

a. adding one of an amine and an acid to the reaction mixture,
b. adding a polar liquid to the mixture obtained in step a) to induce phase separation and formation of a polar phase and a separate organic phase, the organic phase containing the halogenated alkoxyethane, and
c. adding the other of the amine and the acid not used step a) to the organic phase obtained in step b) to thereby purify the halogenated alkoxyethane.

As used herein, the expression "reaction mixture" refers to a mixture of products derived from the batch wise synthesis of the halogenated alkoxyethane. It will therefore be understood that said reaction mixture would be one that comprises the halogenated alkoxyethane.

By the process being one for "purifying" halogenated alkoxyethane is meant that the process affords removal of impurities from the reaction mixture, for example impurities of the kind described herein, resulting in a mixture having less amount of impurities relative to the reaction mixture.

The sequence of steps a) and c) in the process of the invention has surprisingly been found effective to facilitate the purification of the halogenated alkoxyethane to obtain pharmaceutical grade halogenated alkoxyethane produced in a batch synthesis procedure.

Accordingly, in some embodiments the process of the invention further comprises a step d) of isolating the purified halogenated alkoxyethane. Step d) can advantageously provide for isolation of pharmaceutical grade halogenated alkoxyethane. As used herein in relation to the halogenated alkoxyethane, the expression "pharmaceutical grade" means that the halogenated alkoxyethane is at least 99% purity (e.g. about 99.9% purity).

Without wanting to be limited by theory, it is postulated that the amine and the acid added in accordance to the invention can efficiently convert impurities present in the reaction mixture into compounds that are more amenable to removal, while remaining inert towards the halogenated alkoxyethane. Accordingly, the proposed treatment can advantageously replace or complement existing purification routes based on physical separation, such as fractional distillation, for the production of pharmaceutical grade halogenated alkoxyethane compounds.

The process of the invention is performed on a reaction mixture which is derived from a batch synthetic procedure for producing the halogenated alkoxyethane. By being a "batch" synthetic procedure for producing halogenated alkoxyethane, the procedure is one in which the intended amount of all reagents used to synthesise the halogenated alkoxyethane is loaded at once or sequentially into a reactor vessel, where they react under predetermined reaction conditions with no additional reagent added into the reaction system as the reaction proceeds. This is opposed to semi-continuous or continuous synthetic procedures, in which one or more reagents are introduced into the reaction system continuously as the reaction proceeds. Examples of said procedures include reactions performed in chemical flow reactors.

In some embodiments, the halogenated alkoxyethane is produced using a precursor compound selected from (i) a compound of general formula XClHC—$CYF_2$, where each of X and Y is independently —Cl or —F, and (ii) a compound of general formula XClC═$CF_2$ where X is —Cl or —F. An example of a suitable compound of general formula XClC═$CF_2$ may be $Cl_2C$═$CF_2$, and an example of a suitable compound of general formula XClHC—$CYF_2$ may be $Cl_2HC$—$CF_3$. In those instances, the halogenated alkoxyethane may be a compound of commercial interest such as methoxyflurane.

The present invention also provides a halogenated alkoxyethane of general formula XClHC—$CF_2$OR, where X is —Cl or —F and OR is $C_{1-4}$ alkoxy, purified in accordance with the process of the invention, the halogenated alkoxyethane having purity of at least 99%.

Further aspects and embodiments of the invention are discussed in more detail below.

BRIEF DESCRIPTION OF THE DRAWINGS

The invention will also be described herein with reference to the following non-limiting drawings in which.

DETAILED DESCRIPTION OF THE INVENTION

Figure 1:
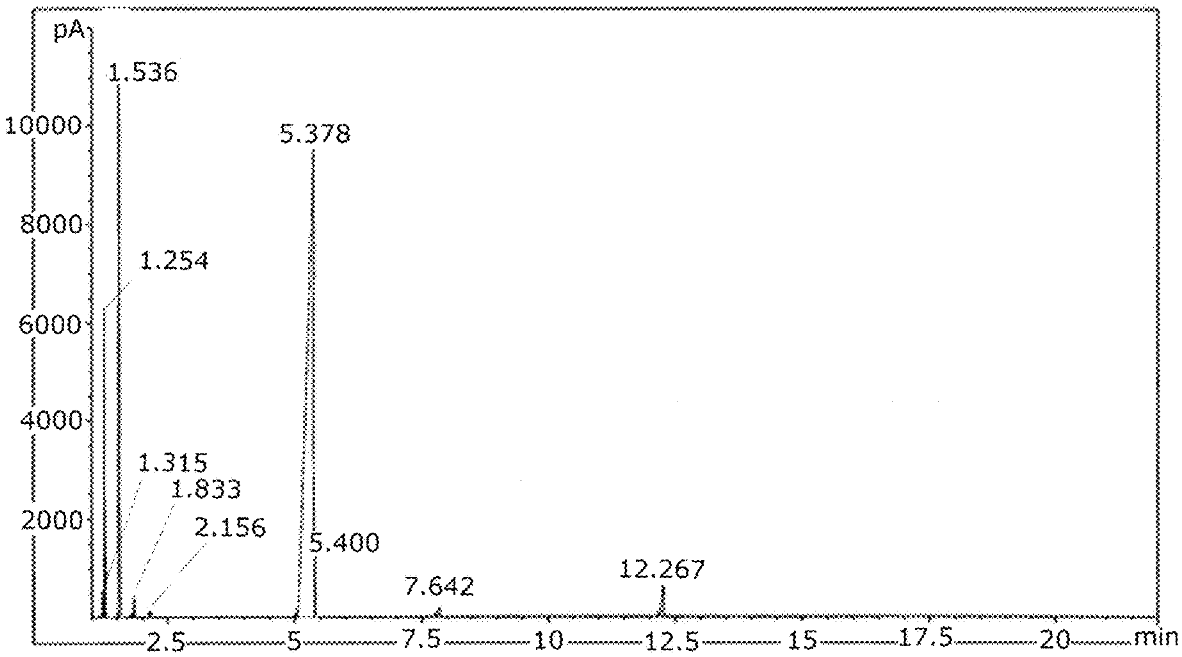
FIG. 1 shows a gas chromatography (GC) trace of a mixture containing methoxyflurane before undergoing purification.
Figure 2:
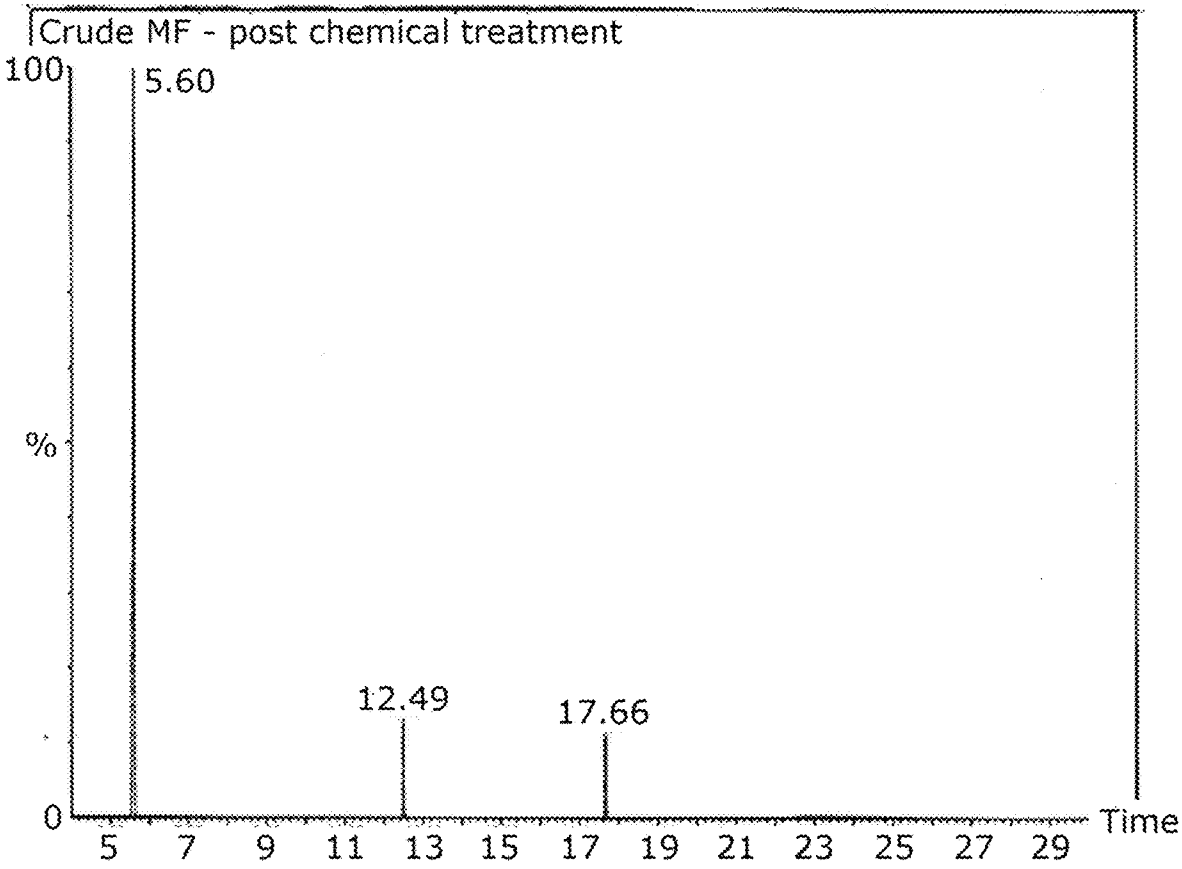
FIG. 2 shows a gas chromatography (GC) trace of purified methoxyflurane in accordance with an embodiment procedure of the invention.

The process of the invention is one for purifying halogenated alkoxyethane of general formula XClHC—$CF_2$OR, where X is —Cl or —F and OR is $C_{1-4}$ alkoxy.

As used herein, the expression "$C_{1-4}$ alkoxy" denotes a straight chain or branched alkoxy group having from 1 to 4 carbons. Examples of straight chain and branched alkoxy include methoxy, ethoxy, n-propoxy, isopropoxy, n-butoxy, sec-butoxy, and t-butoxy.

In the process of the invention, the halogenated alkoxyethane is purified from a reaction mixture derived from a batch synthetic procedure for producing the halogenated alkoxyethane. Said batch synthetic procedure may be one in which the halogenated alkoxyethane is produced using a precursor compound selected from (i) a compound of general formula $XClHC—CYF_2$, where each of X and Y is independently —Cl or —F, and (ii) a compound of general formula $XClC{=}CF_2$ where X is —Cl or —F.

For instance, the batch synthetic procedure for producing the halogenated alkoxyethane may be one that involves reacting either of (i) the compound of general formula $XClHC—CYF_2$, where each of X and Y is independently —Cl or —F, or (ii) the compound of general formula $XClC{=}CF_2$ where X is —Cl or —F, with a base and a $C_{1-4}$ alkanol.

The base used in a batch synthetic procedure for producing the halogenated alkoxyethane may be any base that can promote the addition reaction of the $C_{1-4}$ alkanol to (i) the compound of general formula $XClHC—CYF_2$, where each of X and Y is independently —Cl or —F, or (ii) the compound of general formula $XClC{=}CF_2$ where X is —Cl or —F. In some embodiments, the base comprises an alkali metal base cation. For example, the base may be selected from the group consisting of an alkali metal (e.g. Li, Na and K) salt, an alkali metal salt (e.g. carbonates, phosphates), an alkali metal hydroxide, an alkali metal alkoxide (e.g. methylate, ethylate, phenolate), and a combination thereof. For example, the base may be selected from sodium methoxide, and potassium methoxide. In some embodiments, the base is an alkali metal hydroxide of general formula M-OH, wherein M is an alkali metal selected from the group consisting of Li, Na and K. In some embodiments, the alkali metal hydroxide is NaOH or KOH. In some embodiments, the base is KOH. In some embodiments, the base comprises an ammonium or phosphonium base cation. Examples of suitable such bases include tetrabutylammonium hydroxide, benzyl(trimethyl)ammonium hydroxide, N-methyl-N,N,N-trioctylammonium chloride (Aliquat 336), tetraethylammonium hydroxide, tetramethylammonium hydroxide, and tetramethylphosphonium hydroxide.

The $C_{1-4}$ alkanol may be any $C_{1-4}$ alkanol that can promote addition of a $C_{1-4}$ alkoxy group to the second carbon of the compound of general formula $XClHC—CYF_2$, or that can promote addition reaction to the C═C bond of the compound of general formula $XClC{=}CF_2$, resulting in a $C_{1-4}$ alkoxy group bonded on the second carbon. In some embodiments, the $C_{1-4}$ alkanol is selected from methanol ($CH_3OH$), ethanol ($CH_3CH_2OH$), 1-propanol ($CH_3CH_2CH_2OH$), 2-propanol ($(CH_3)_2CHOH$), 1-butanol ($CH_3CH_2CH_2CH_2OH$), 2-butanol ($CH_3CH_2CHOHCH_3$), 2-methyl-1-propanol ($(CH_3)_2CHCH_2OH$), 2-methyl-2-propanol ($(CH_3)_3COH$), and a combination thereof. In some embodiments, the $C_{1-4}$ alkanol is methanol.

In some embodiments, the compound of general formula $XClHC—CYF_2$ used in the batch synthetic procedure for producing the halogenated alkoxyethane is $Cl_2HC—CF_3$, or the compound of general formula $XClC{=}CF_2$ used in the batch synthetic procedure for producing the halogenated alkoxyethane is $C_{12}C{=}CF_2$. In those instances, if methanol is used as the $C_{1-4}$ alkanol the resulting halogenated alkoxyethane is methoxyflurane.

Accordingly, in some embodiments the halogenated alkoxyethane is methoxyflurane.

Those instances are particularly advantageous since methoxyflurane is the active ingredient of Penthrox®, which is an effective and rapid-onset short-term analgesic for the initial management of acute trauma pain and brief painful procedures such as wound dressing. Penthrox® is an analgesic used by medical practitioners, the defence forces, ambulance paramedics, sports clubs and surf lifesavers to administer emergency pain relief through inhaler devices known as "Green Whistles".

Penthrox® has received Regulatory Approvals in a number of major jurisdictions worldwide, and is expected to be ubiquitously available in disposable, single-use inhaler devices allowing patients (including children) to self-administer the drug under supervision. Current testing is being performed on advanced inhalers for the self-administration of Penthrox® to be marketed in addition to the Green Whistles. The test inhalers have been developed to be fully integrated pain release systems delivering about 3 ml of Penthrox® to patients in a quick and easy manner. The test inhaler comprises a lock out tab, a plunger that activates the inhaler, and a mouthpiece though which the user can inhale the active Penthrox® composition by normal breathing. Once the lock out tab is removed, the inhaler can be activated by pushing down the plunger. The inhaler would then be set to release the active ingredient through the mouthpiece by the user simply inhaling.

Penthrox® is aimed at becoming available worldwide in facilities that (i) can provide first-aid and emergency services (e.g. hospital emergency, ambulance services, lifesaving clubs, etc.), (ii) necessitate mobile, agile, and point-of-care first-aid and emergency services (e.g. the military), and (iii) can market Penthrox® to the general public (e.g. pharmacies) as a mainstream analgesic of choice.

Accordingly, the process of the present invention can be particularly advantageous for the purification of crude batch reaction mixtures comprising methoxyflurane to provide pharmaceutical grade methoxyflurane.

In some embodiments, the compound of general formula $XClHC—CYF_2$ used in the batch synthetic procedure for producing the halogenated alkoxyethane is $FClHC—CF_3$, or the compound of general formula $XClC{=}CF_2$ used in the batch synthetic procedure for producing the halogenated alkoxyethane is $FClC{=}CF_2$. In those instances, if the $C_{1-4}$ alkanol is methanol the resulting halogenated alkoxyethane is $ClFHC—CF_2OCH_3$ (2-chloro-1,1,2-trifluoroethylmethyl ether).

Accordingly, in some embodiments the halogenated alkoxyethane is $ClFHC—CF_2OCH_3$ (2-chloro-1,1,2-trifluoroethylmethyl ether).

The possibility to produce highly pure and high amounts of $ClFHC—CF_2OCH_3$ can be particularly advantageous, since that compound is a known precursor in the synthesis of the inhalant anaesthetic enflurane (2-chloro-1,1,2,-trifluoroethyl-difluoromethyl ether). Accordingly, the process of the present invention is particularly advantageous for the purification of crude batch reaction mixtures comprising $ClFHC—CF_2OCH_3$ to provide pharmaceutical grade $ClFHC—CF_2OCH_3$ and eventually enflurane.

The process of the invention is for purifying halogenated alkoxyethane from a reaction mixture derived from a batch synthetic procedure for producing the halogenated alkoxyethane. Said reaction mixture may comprise, in addition to the halogenated alkoxyethane, undesired impurities. As such, the process of the invention may also be said to be one that facilitates removal of impurities from a reaction mixture derived from a batch synthetic procedure for producing the halogenated alkoxyethane. Depending on the synthesis conditions and/or the nature of the precursor compounds used in the batch synthetic procedure for producing the halogenated alkoxyethane, said impurities may comprise one or more reaction by-product(s) and/or one or more unreacted precursor compounds.

For example, when the halogenated alkoxyethane is methoxyflurane obtained by reacting $Cl_2HC—CF_3$ or $Cl_2C═CF_2$ with a base (for example a base of the kind described herein) and methanol, the impurities in the resulting reaction mixture may comprise one or more of methanol, dichloro-difluoroethylene (DCDFE), 2,2-dichloro-1,1,1-trifluoroethane, ethers (for example vinyl ethers such as methoxyethene (ME), 1,1-dichloro-2-fluoro-2-methoxyethene, halomar (2-chloro-1,1,2-trifluoroethyl methyl ether)), orthoesters (OE) such as 2,2-dichloro-1,1,1-trimethoxyethane, methyl dichloroacetate (MDA), chloroform, and HF. Scheme 1 below shows the postulated mechanisms involving formation of some of those impurities through further reactions of methoxyflurane in the reaction mixture.

Scheme 1 Postulated mechanism of formation of impurities from methoxyflurane

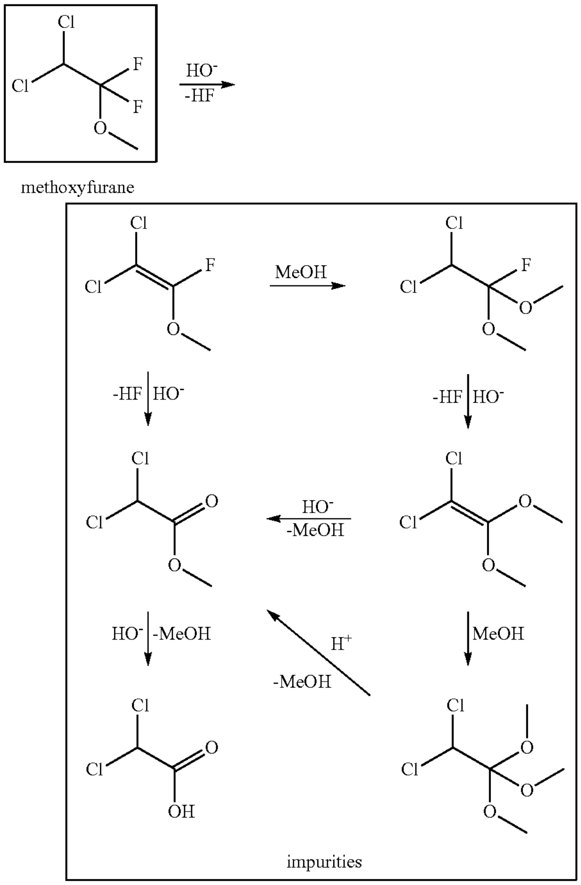

Accordingly, in some embodiments the process is one for purifying the halogenated alkoxyethane from impurities comprising one or more of methanol, 2,2-dichloro-1,1,1-trifluoroethane, methyl dichloroacetate, 1,1-dichloro-2,2-difluoroethylene, chloroform, hydrogen fluoride and methoxyethene (ME), orthoesters (OE) such as 2,2-dichloro-1,1,1-trimethoxyethane, and methyl dichloroacetate (MDA).

Advantageously, the process of the invention can facilitate removal of impurities from a reaction mixture comprising the halogenated alkoxyethane irrespective of the amount of impurities present in the reaction mixture. For example, the reaction mixture may contain an amount of impurities of up to about 30% by volume of the mixture. In some embodiments, the reaction mixture contains an amount of impurities of less than about 20%, less than about 15%, less than about 10%, less than about 5%, less than about 2.5%, or less than about 1% by volume of the mixture. In some embodiments, the reaction mixture contains an amount of impurities of less than 5% by volume of the mixture.

The process of the invention may be integrated into a batch reactor system used to produce halogenated alkoxyethane. For instance, the process may be integrated into a batch reactor system for the synthesis of halogenated alkoxyethane as a post-synthesis purification procedure.

In some embodiments, the purification procedure of the invention is performed directly on a crude batch reaction mixture containing the halogenated alkoxyethane. In those instances, said crude batch reaction mixture is the reaction mixture according to the invention.

In some embodiments, the reaction mixture of the invention derives from a crude batch reactor mixture. In those instances, the crude batch reactor mixture undergoes further processing resulting in the reaction mixture of the invention. For example, the crude batch reaction mixture may first undergo a phase separation procedure. Said procedure may involve the addition of a polar liquid to the crude batch reactor mixture to form a biphasic mixture made of a polar phase and a separate organic phase comprising the halogenated alkoxyethane. In those instances, the organic phase would then be separated from the polar phase, which can be discarded, before further processing.

Accordingly, in some embodiments the process further comprises steps of mixing a crude batch reaction mixture with a polar liquid to induce phase separation between a polar phase and a separate organic phase, and separating said organic phase from the polar phase, wherein the separate organic phase is the reaction mixture comprising the halogenated alkoxyethane according to the invention.

In the context of the invention, separation of a polar phase from a separate organic phase in a biphasic mixture may be effected according to any means known to the skilled person. For example, said separation may be effected by way of a gravity separator (e.g. a phase separation flask, tank, or a separating funnel), a super-hydrophobic mesh, a super-oleophobic mesh, and the like. A skilled person would be capable to identify suitable means and procedures for the effective separation of the phases of a biphasic mixture.

As used herein, a "polar liquid" is a liquid substance that can be added to a mixture comprising a halogenated alkoxyethane of the kind described herein, resulting in the formation of a biphasic mixture comprising a polar phase and a separate organic phase containing the halogenated alkoxyethane. An example of a suitable polar liquid in that regard is water.

The process of the invention comprises a step a) of adding one of an amine and an acid to the reaction mixture. By "adding one of an amine and an acid to the reaction mixture" is meant that either an amine or an acid is added to the reaction mixture. Accordingly, in some embodiments the process of the invention comprises adding an amine to the reaction mixture. In some embodiments, the purification procedure comprises adding an acid to the reaction mixture. The amine or the acid may be an amine or an acid of the kind described herein.

In some embodiments, step a) comprises adding an amine to the reaction mixture.

Without wanting to be limited by theory, it is believed that an amine of the kind described herein can react with impurities present in the reaction mixture through N-alkylation and/or amidation routes. This advantageously converts the impurities into compounds that are more amenable to removal in the isolation step than the starting impurities.

For example, a batch synthetic procedure for producing methoxyflurane of the kind described herein can lead to the formation of 1,1-dichloro-2-fluoro-2-methoxyethene (vinyl ether) and/or methyl dichloroacetate impurities. In those instances, 1,1-dichloro-2-fluoro-2-methoxyethene (vinyl ether) can react with primary and/or secondary amines through N-methylation, providing 2,2-dichloroacetyl fluoride. Both 2,2-dichloroacetyl fluoride and methyl dichloroacetate may react further with primary and/or secondary amines through amidation routes to produce corresponding dichloroacetamides. The resulting dichloroacetamides are more amenable to removal in the isolation step. A schematic of those reactions is shown in Scheme 2.

Scheme 2 postulated mechanism route of the chemical removal of 1,1-dichloro-2-fluoro-2-methoxyethane (vinyl ether), and methyl dichloroacetate impurites during purification of methoxyflurane.

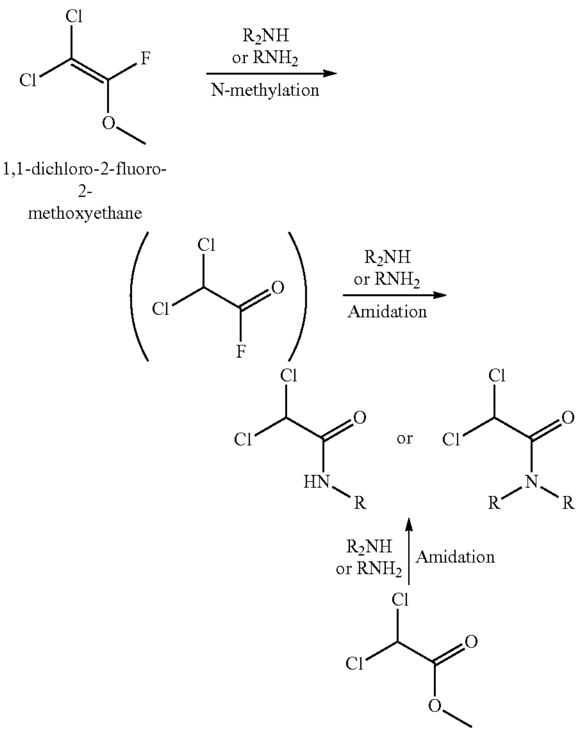

1,1-dichloro-2-fluoro-2-methoxyethane or methyl 2,2-dichloroacetate

The amine may be a primary or a secondary amine.

Examples of amines suitable for use in the process of the invention include ethylenediamine (1,2-diaminoethane), 1,3-diaminopropane, diethylenetriamine, di-n-propylamine, n-butylamine, ethanolamine, pyrrolidine, 2-aminobutane, and a mixture thereof. In some embodiments, the amine is selected from ethylenediamine, 1,3-diaminopropane, diethylenetriamine, and a mixture thereof.

In some embodiments, step a) comprises adding an acid to the reaction mixture.

Examples of suitable acids include citric acid, hydrochloric acid, sulfuric acid, *sulphurous* acid, methanesulfonic acid, trifluoromethanesulfonic acid, phosphoric acid, acetic acid, trifluoroacetic acid, nitric acid, nitrous acid, hypochlorous acid, chlorous acid, chloric acid, perchloric acid, and a combination thereof. In one embodiment, the acid is methanesulfonic acid (MSA).

The acid may be added in any form that would be suitable to promote effective reaction with impurities present in the reaction mixture. For example, the acid may be in the form of an acid solution, such as an aqueous acid solution.

In some embodiments, the acid is at least a 10%, at least a 20%, at least at 30%, or at least a 40% acid solution.

In step a), the amine or the acid may be added to the reaction mixture according to any effective amount that is fit for the intended purpose. In some embodiments, the amine or the acid are added to the reaction mixture according to a volume ratio from about 0.05:1 to about 2:1 (amine or acid:reaction mixture). In some embodiments, the amine or the acid are added to the reaction mixture according to a volume ratio of about 0.1:1, about 0.25:1, about 0.5:1, about 1:1, or about 2:1 (amine or acid:reaction mixture).

Step a) may be performed in any manner that is effective to promote reaction between one or more impurities and the amine or the acid. For example, addition of the amine or the acid may be performed as a batch procedure or as a continuous procedure.

Once the amine or the acid is added to the reaction mixture in step a), the resulting mixture can be let react for any duration of time conducive to effective reaction between one or more impurities and the amine or the acid. For example, the mixture obtained in step a) may be let react for at least about 1 minute. In some embodiments, the mixture obtained in step a) is let react for at least about 5 minutes, at least about 15 minutes, at least about 30 minutes, at least about 60 minutes, or at least about 2 hours. During reaction, the mixture may be kept under constant stirring.

Addition of the amine or the acid to the reaction mixture in step a) may be performed at any temperature conducive to effective reaction between one or more impurities and the amine or the acid. For example, the amine or the acid may be added to the reaction mixture at a temperature of from about 10° C. to about 120° C. High addition temperatures (e.g. up to 120° C.) may facilitate separation of more volatile impurities. In some embodiments, the amine or the acid is added to the reaction mixture at a temperature of from about 10° C. to about 50° C. In some embodiments, the amine or the acid in step a) is added to the reaction mixture at room temperature. The resulting mixture may be kept at a temperature that is conducive to effective reaction between one or more impurities and the amine or the acid. For example, the resulting mixture may be kept at a temperature of from about 10° C. to about 50° C. In some instances, reaction between impurities and the amine or the acid can be exothermic, in which case following addition of the amine or the acids the temperature of the resulting mixture may be observed to increase gradually as the amine or the acid are added.

The process of the invention also comprises a step b) of adding a polar liquid to the mixture obtained in step a). This results in formation of a biphasic mixture made of a polar phase and a separate organic phase, in which the separate organic phase contains the halogenated alkoxyethane.

The polar liquid may be a polar liquid of the kind described herein. For example, the polar liquid used in step b) may be water. In those instances, the polar phase in step b) would be an aqueous phase.

In step b), the polar liquid may be added to the mixture obtained in step a) in any amount suitable to induce the required phase separation and formation of a polar phase and a separated organic phase. For example, the polar liquid may be added to the mixture obtained in step a) according to a volume ratio from about 0.5:1 to about 2:1 (polar liquid: mixture). In some embodiments, the polar liquid is added to the mixture obtained in step a) according to a volume ratio of about 0.5:1, about 1:1, about 1.5:1, or about 2:1 (polar liquid:mixture).

Once the polar liquid is added in step b) to the mixture obtained in step a), the resulting biphasic mixture may be maintained under stirring for any duration of time conducive to the dissolution of polar impurities present in the starting mixture into the polar phase. For example, the resulting biphasic mixture may be kept under constant stirring for at least about 5 minutes, at least about 15 minutes, at least about 30 minutes, or at least about 60 minutes.

In some embodiments, step b) is followed by a step of separating the organic phase obtained in step b) from the polar phase before further processing. Separation may be effected according to any procedure known to a skilled person which would be fit for the intended purpose. For example, separation may be effected by means of the kind described herein. In those instances, the separated polar phase is discarded.

The process of the invention also comprises a step c) of adding the other of the amine and the acid of step a) to the organic phase obtained in step b).

By the expression "the other of the amine and the acid not used in step a)" is meant that if the amine is used in step a), then the acid is used in step c). Vice versa, if the acid is used in step a), then the amine is used in step c).

In some embodiments, the process of the invention comprises adding an amine to the reaction mixture, and a subsequent addition of an acid to the resulting mixture. The amine or the acid may be an amine or an acid of the kind described herein.

In some embodiments, the process of the invention comprises adding an acid to the reaction mixture, and a subsequent addition of an amine to the resulting mixture. The amine or the acid may be an amine or an acid of the kind described herein.

Accordingly, in some embodiments the process comprises the steps of:

i. adding an amine to the reaction mixture,
ii. adding a polar liquid to the mixture obtained in step i) to induce phase separation and formation of a polar phase and a separate organic phase, the organic phase containing the halogenated alkoxyethane, and
iii. adding an acid to the organic phase obtained in step ii).

In some alternative embodiments, the process comprises the steps of:

i. adding an acid to the reaction mixture,
ii. adding a polar liquid to the mixture obtained in step i) to induce phase separation and formation of a polar phase and a separate organic phase, the organic phase containing the halogenated alkoxyethane, and
iii. adding an amine to the organic phase obtained in step ii).

It will be understood that the amine and the acid would be an amine and an acid of the kind described herein, and that any process conditions would be a process condition of the kind described herein.

In step c), adding the other of the amine and the acid not used in step a) to the organic phase obtained in step b) is advantageous to convert impurities that could not be converted in step a), and/or eliminate undesired by-product impurities generated by reactions promoted in step a).

For example, when step a) comprises adding an acid to the reaction mixture, ethane impurities (if present in the reaction mixture) may convert to the corresponding chloroacetates, which may impact the isolation of the purified halogenated alkoxyethane resulting in formation of further acidic by-product impurities. In turn, this may lead to contamination of the final product by chloroacetates. For instance, under acidic conditions the by-product 2,2-dichloro-1,1,1-timethoxyethane may be converted to methyl dichloroacetate as summarised in Scheme 3 below.

Scheme 3 Conversion of 2,2-dichloro-1,1,1-trimethoxyethane dichloroacetate

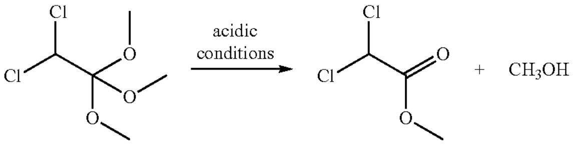

2,2-dichloro-1,1,1-trimethoxyethane

In those instances, the amine added in step c) can react with the chloroacetates through amidation routes to produce corresponding dichloroacetamides, which are more amenable to removal in the isolation step.

In step c), the amine or the acid may be added to the organic phase obtained in step b) according to any effective amount that is fit for the intended purpose. In some embodiments, the amine or the acid are added to the organic phase obtained in step b) according to a volume ratio from about 0.05:1 to about 2:1 (amine or acid:organic phase). In some embodiments, the amine or the acid are added to the organic phase obtained in step b) according to a volume ratio of about 0.1:1, about 0.25:1, about 0.5:1, about 1:1, or about 2:1 (amine or acid:organic phase).

Step c) may be performed in any manner that is effective to promote reaction between one or more impurities and the amine or the acid. For example, addition of the amine or the acid to the organic phase obtained in step b) may be performed as a batch procedure or as a continuous procedure.

As a skilled person would appreciate, the addition of the amine or the acid to the organic phase obtained in step b) may require first separating said organic phase from the polar phase obtained in step b). For instance, when the amine or the acid used in step c) may react dangerously with the polar phase obtained in step b), the organic phase and said polar phase would have to be first separated. Phase separation may be achieved in accordance to any procedure of the kind described herein.

In step c), once the amine or the acid is added to the organic phase of step b), the resulting mixture can be let react for any duration of time conducive to effective reaction between one or more impurities and the amine or the acid. For example, the mixture obtained in step c) may be let react for at least about 1 minute. In some embodiments, the mixture obtained in step c) is let react for at least about 5 minutes, at least about 15 minutes, at least about 30 minutes, at least about 60 minutes, or at least about 2 hours. During reaction, the mixture may be kept under constant stirring.

Addition of the amine or the acid in step c) may be performed at any temperature conducive to effective reaction between one or more impurities and the amine or the acid. For example, the amine or the acid in step c) may be added to the reaction mixture at a temperature of from about 10° C. to about 120° C. High addition temperatures (e.g. up to 120° C.) may facilitate separation of more volatile impurities. In some embodiments, the amine or the acid is added in step c) at a temperature of from about 10° C. to about 50° C. In some embodiments, the amine or the acid in step c) are added at room temperature. The resulting mixture may be kept at a temperature that is conducive to effective reaction between one or more impurities and the amine or the acid. For example, the resulting mixture may be kept at a temperature of from about 10° C. to about 50° C.

Advantageously, the amine or the acid used in accordance to the process of the invention can react particularly effectively with impurities while remaining inert towards the halogenated alkoxyethane.

For example, in the purification procedure to obtain pharmaceutical grade methoxyflurane, an amine of the kind described herein is particularly effective to react selectively with low component impurity (e.g. methyl dichloroactetate) while retaining methoxyflurane. This has been found to be particularly advantageous for further isolation of methoxyflurane above 99% purity, for example at about 99.9% purity.

In a particularly advantageous purification procedure for methoxyflurane, step a) of the purification process comprises adding an acid to the reaction mixture, and step c) of the purification process comprises adding an amine to the organic phase obtained in step b). For instance, step a) of the purification process for methoxyflurane may comprise adding methane sulfonic acid to the reaction mixture, and step c) of the purification process may comprises adding ethanolamine to the organic phase obtained in step b). Accordingly, in some embodiments the process is one for the production of methoxyflurane, and includes a purification process comprising adding and acid (e.g. methane sulfonic acid) to the reaction mixture, and a subsequent addition of an amine (e.g. ethanolamine) to a resulting mixture.

Since the amine and the acid remain inert towards the halogenated alkoxyethane, the process of the invention can be performed using excess of amine and acid relative to the amount of impurities present in the relevant mixtures. Accordingly, any differences in the level of impurities depending on the specific batch synthesis procedure used to produce the halogenated alkoxyethane can be advantageously accommodated.

In a typical batch procedure, a crude batch reaction mixture contains halogenated alkoxyethane at a purity of less than 70%. Advantageously, following step c), the process of the invention can advantageously provide purified halogenated alkoxyethane at a purity of not less than 70%. For example, following step c) the process of the invention affords halogenated alkoxyethane at a purity of at least 70%, at least 75%, at least 85%, or at least 90%.

In short, the process of the invention can facilitate removal of impurities from a reaction mixture comprising the halogenated alkoxyethane irrespective of the amount of impurities present in the reaction mixture. This is particularly advantageous when the batch reaction synthesis of halogenated alkoxyethane is limited by poor conversion yields. In those instances, the purification procedure of the invention can greatly assist to provide pharmaceutical grade halogenated alkoxyethane.

In some embodiments, the process comprises a step of adding a polar liquid to the mixture obtained in step c). This induces a phase separation between a polar phase and a separate organic phase, the organic phase comprising the halogenated alkoxyethane. In some embodiments, said organic phase may be separated from the polar phase before further processing. Separation may be effected according to any procedure known to a skilled person which would be fit for the intended purpose. For example, separation may be effected by means of the kind described herein. In these instances, the separated polar phase is discarded.

Following a separation step of the kind described herein, the separated organic phase may undergo drying before being processed further. For example, a separated organic phase of the kind described herein may be dried with a desiccant. Examples of suitable desiccants in that regard include inorganic desiccants such as magnesium sulfate.

Accordingly, in some embodiments, the organic phase separated from the polar phase following addition of a polar liquid to the mixture obtained in step c) is dried with a desiccant before further processing. The desiccant may be magnesium sulfate.

In some embodiments, the process of the invention further comprises a step d) of isolating the purified halogenated alkoxyethane. The step may be performed on a dried organic phase obtained from the mixture of step c) in accordance to a phase separation procedure of the kind described herein.

In step d), the purified halogenated alkoxyethane may be isolated by any suitable means known to a skilled person that would result in halogenated alkoxyethane with purity of at least 95%, for example at least 99%, such as about 99.9%.

For example, the purified halogenated alkoxyethane may be isolated by distillation. A skilled person would be able to readily identify suitable distillation conditions affording isolation of the halogenated alkoxyethane, for example based on the physical characteristics of the specific halogenated alkoxyethane and the nature and amount of any residual impurities.

In some embodiments, isolation of the purified halogenated alkoxyethane is performed by fractional distillation. Those embodiments are particularly advantageous for the isolation of purified methoxyflurane obtained by reacting $Cl_2C{=}CF_2$ with a base of the kind described herein and methanol.

In some embodiments, isolation of the purified halogenated alkoxyethane comprises flash distillation. The flash distillation would be effective to remove impurities that are significantly more volatile than the halogenated alkoxyethane. Those impurities may include, for example, unreacted alkanol and/or unreacted precursor compound.

In some embodiments, isolation of the purified halogenated alkoxyethane is performed by subsequent distillations.

For example, isolation of the purified halogenated alkoxyethane may be performed by first conducting a flash distillation to obtain a halogenated alkoxyethane-rich bottoms liquid, followed by distillation of said bottoms liquid to obtain the isolated purified halogenated alkoxyethane. The flash distillation would be effective to remove impurities that are significantly more volatile than the halogenated alkoxyethane. Those impurities may include, for example, unreacted alkanol and/or unreacted precursor compound. Said flash distillation may be performed on a halogenated alkoxyethane-rich mixture deriving from step c). For instance, said flash distillation may be performed on a dried halogenated alkoxyethane-rich organic phase obtained by phase-separating a mixture obtained in step c). The subsequent distillation of the halogenated alkoxyethane-rich bottoms liquid would readily provide the isolated purified halogenated alkoxyethane.

A skilled person would be able to readily identify suitable distillation conditions in those instances where isolation of the purified halogenated alkoxyethane in step d) of the purification procedure is performed by subsequent distillations. For instance, the flash distillation may be performed at a temperature below the boiling point of the halogenated alkoxyethane, yet sufficiently high that more volatile impurities evaporate preferentially. In some embodiments, flash distillation is performed at a temperature from about 30° C. to about 90° C., for example from about 35° C. to about 60° C. Subsequent distillation of the halogenated alkoxyethane-rich bottoms liquid may be performed at a temperature above the boiling point of the halogenated alkoxyethane. In some embodiments, the distillation is performed at a temperature above 100° C.

Embodiments in which isolation of the purified halogenated alkoxyethane by a sequence of flash distillation and fractional distillation are particularly advantageous for the isolation of methoxyflurane obtained by reacting $Cl_2HC—CF_3$ with a base of the kind described herein and methanol.

Since the performance of step d) can afford obtaining pharmaceutical grade halogenated alkoxyethane, the present invention may also be said to provide a process for purifying halogenated alkoxyethane of general formula $XClHC—CF_2OR$, where X is —Cl or —F and OR is $C_{1-4}$ alkoxy, from a reaction mixture derived from a batch synthetic procedure for producing the halogenated alkoxyethane, the process comprising the steps of:

a. adding one of an amine and an acid to the reaction mixture,
b. adding a polar liquid to the mixture obtained in step a) to induce phase separation and formation of a polar phase and a separate organic phase, the organic phase containing the halogenated alkoxyethane,
c. adding the other one of the amine and the acid not used in step a) to the organic phase obtained in step b), and
d. isolating the purified halogenated alkoxyethane.

In some embodiments, the process comprises a sequence of steps of the kind described herein.

Accordingly, in some embodiments the process comprises the steps of:

i. adding an amine to the reaction mixture,
ii. adding a polar liquid to the mixture obtained in step i) to induce phase separation and formation of a polar phase and a separate organic phase, the organic phase containing the halogenated alkoxyethane,
iii. adding an acid to the organic phase obtained in step ii), and
iv. isolating the purified halogenated alkoxyethane.

In some alternative embodiments, the process comprises the steps of:

i. adding an acid to the reaction mixture,
ii. adding a polar liquid to the mixture obtained in step i) to induce phase separation and formation of a polar phase and a separate organic phase, the organic phase containing the halogenated alkoxyethane,
iii. adding an amine to the organic phase obtained in step ii), and
iv. isolating the purified halogenated alkoxyethane.

Accordingly, in some embodiments the process of the invention comprises the steps of:

i. adding a polar liquid to a crude reaction mixture obtained from a batch synthetic procedure for producing the halogenated alkoxyethane, to induce phase separation and formation of a polar phase and a separate organic phase comprising the halogenated alkoxyethane,
ii. separating the organic phase obtained in step i),
iii. adding one of the amine and the acid to the organic phase obtained in step ii),
iv. adding a polar liquid to the mixture obtained in step iii) to induce phase separation and formation of a polar phase and a separate organic phase, the organic phase containing the halogenated alkoxyethane,
V. separating the organic phase obtained in step iv),
vi. adding the other of the amine and the acid not used in step iii) to the organic phase obtained in step v),
vii. adding a polar liquid to the mixture obtained in step vi), to induce phase separation and formation of a polar phase and a separate organic phase, the organic phase containing the halogenated alkoxyethane,
viii. separating the organic phase obtained in step vii),
ix. drying the organic phase obtained in step viii),
X. performing flash distillation on the organic phase obtained in step ix) to obtain a halogenated alkoxyethane-rich bottoms liquid, and
xi. distilling the halogenated alkoxyethane-rich bottoms liquid obtained in step x) by fractional distillation, thereby isolating the purified halogenated alkoxyethane.

It will be understood that all compounds and process conditions of steps i)-xi) listed in the preceding paragraph are compounds and process conditions of the kind described herein.

Embodiments having a sequence of said steps i)-xi) are particularly advantageous for the purification of methoxyflurane obtained by reacting $Cl_2HC—CF_3$ with a base of the kind described herein and methanol.

In some embodiments the process of the invention comprises the steps of:

i. adding a polar liquid to a crude reaction mixture obtained from a batch synthetic procedure for producing the halogenated alkoxyethane, to induce phase separation between a polar phase and a separate organic phase comprising the halogenated alkoxyethane,
ii. separating the organic phase obtained in step i),
iii. adding one of the amine and the acid to the organic phase obtained in step ii),
iv. adding a polar liquid to the mixture obtained in step iii) to induce phase separation and formation of a polar phase and a separate organic phase, the organic phase containing the halogenated alkoxyethane,
V. separating the organic phase obtained in step iv),
vi. adding the other of the amine and the acid not used in step iii) to the organic phase obtained in step v),
vii. adding a polar liquid to the mixture obtained in step vi), to induce phase separation and formation of a polar phase and a separate organic phase, the organic phase containing the halogenated alkoxyethane,
viii. separating the organic phase obtained in step vii),
ix. drying the organic phase obtained in step viii), and
x. distilling the organic phase obtained in step ix) by fractional distillation, thereby isolating the purified halogenated alkoxyethane.

It will be understood that all compounds and process conditions of steps i)-x) listed in the preceding paragraph are compounds and process conditions of the kind described herein. Embodiments having a sequence of said steps i)-x)

are particularly advantageous for the purification of methoxyflurane obtained by reacting $Cl_2C{=}CF_2$ with a base of the kind described herein and methanol.

Specific embodiments of the invention will now be described with reference to the following non-limiting examples.

EXAMPLES

Example 1

Methoxyflurane was synthesised as the halogenated alkoxyethane using a batch synthesis procedure. A crude mixture containing methoxyflurane was obtained by reacting $Cl_2CHCF_3$ (HCFC-123, or SUVA-123) with a solution of sodium methoxide ($NaOCH_3$) in methanol, at a temperature of 120° C. Water was added, and the resulting biphasic mixture allowed to stir for a further 30 minutes. The crude product was separated as the bottom layer and dried to afford a clear liquid (Crude A). The composition of said crude batch reaction mixture containing methoxyflurane (Crude A) is shown in Table 1.

Approximately 473 ml (672 g) of Crude A was subsequently transferred to a 1 L flask fitted with a magnetic stirring device and temperature thermometer at ambient temperature (recorded at 20° C.). 50 ml of methanesulphonic acid (MSA) was slowly added to the mixture over approximately 3 minutes while stirring. The temperature was observed to increase from 20° C. to 35° C. during this addition period. The resulting mixture was left to stir for 60 minutes. Subsequently, 400 ml of water was added, and the resulting biphasic mixture allowed to stir for a further 30 minutes.

The biphasic mixture was then transferred to a separating funnel whereby an organic layer containing the methoxyflurane was removed from an aqueous layer. The organic layer was transferred back to the separating flask and washed with a further 400 ml of water, phases separated, and the organic phase transferred back to the 1 L Flask. The composition of said organic phase is shown in Table 1 (Crude B). At this stage no methoxyethene (ME) or orthoester (OE) impurities were detected in the methoxyflurane-rich organic phase (Crude B). However, 4.57% of methyl dichloroacetate (MDA) impurity was detected.

To remove the MDA, Crude B (organic phase rich in methoxyflurane) was treated with ethanolamine. 50 ml of ethanolamine was slowly added to Crude B over approximately 1 minute while stirring at ambient temperature. The resulting mixture was left to stir for approximately 30 minutes. After that, 400 ml of water were added and the stirring stopped to allow phase separation between an organic layer and an aqueous layer. The resulting suspension was then transferred to a separation funnel and the organic layer removed from the aqueous layer. The separated organic phase (again rich in methoxyflurane, Crude C) was dried with a desiccant, magnesium sulphate, and sampled for purity. The final volume was 400 ml (567 g, molar yield based on purification efficiency of 84%, and purity above 74%). The composition of Crude C is shown in Table 1.

Low boiling point impurities (such as methanol and HCFC-123) were subsequently removed from Crude C by flash distillation. Approximately 400 g of Crude C was transferred to a 500 ml vacuum flask set up with a short path distillation column (approximately 300 mm in length) which was in turn connected to a condenser column and a 500 ml fraction collection flask. The methoxyflurane-rich Crude C was then gradually heated under atmospheric pressure until distillate was observed to condense on the condenser and collect in the collection flask (approximately 35-45° C. batch temperature). As the distillate slowed, the temperature of the batch was gradually increased to 60° C. until no more distillate was observed. This was left for approximately 2 hours until the flask was removed from the heat. Analysis by gas chromatography (GC) indicate all methanol and HCFC-123 was removed from the flask, affording a 311.77 g of methoxyflurane as the flash distillation bottoms at a purity above 89%. The composition of said flash distillation bottoms remaining in the flask after flash distillation is shown in Table 1.

TABLE 1

| Composition (%) of mixture containing methoxyflurane during purification steps | | | | | | | |
|---|---|---|---|---|---|---|---|
| CRUDE A | | | | | | | |
| Methanol RTT 0.54 | HCFC-123 RRT 0.58 | Halomar RRT 0.66 | Chloroform RTT 0.75 | MEOF | ME RRT 1.05 | MDA RRT 1.56 | OE RRT 3.30 |
| 1.744 | 19.797 | 0.128 | 0.007 | 68.706 | 1.950 | — | 0.477 |
| Methanol RTT 0.54 | HCFC-123 RRT 0.58 | Halomar RRT 0.66 | | MEOF | ME RRT 1.05 | MDA RRT 1.56 | OE RRT 3.30 |
| CRUDE B - MSA/H2O | | | | | | | |
| 0.906 | 18.572 | 0.131 | 0.016 | 73.083 | — | 4.571 | — |
| CRUDE C - After treatment with ethanolamine and water | | | | | | | |
| 0.795 | 18.155 | 0.133 | 0.009 | 74.112 | — | — | — |

TABLE 1-continued

| Composition (%) of mixture containing methoxyflurane during purification steps | | | | | | | | |
|---|---|---|---|---|---|---|---|---|
| After Flash Distillation | | | | | | | | |
| Methanol RTT 0.54 | HCFC-123 RRT 0.58 | Halomar RRT 0.66 | | MEOF | ME RRT 1.05 | MDA RRT 1.56 | OE RRT 3.30 | Nonane |
| — | — | 0.070 | — | 89.802 | — | — | — | |
| After Final Distillation | | | | | | | | |
| Methanol RTT 0.54 | HCFC-123 RRT 0.58 | Halomar RRT 0.66 | | MEOF | ME RRT 1.05 | MDA RRT 1.56 | OE RRT 3.30 | |
| — | 0.005 | 0.027 | — | 99.81* | 0.016 | — | — | 0.043 |

*mixture contained 0.05% ethoxyflurane from methanol containing a small trace of ethanol. This grade of methanol is not used in the commercial production of methoxyflurane therefore was removed from the GC trace as an impurity.

Even higher purity methoxyflurane was obtained by performing an additional distillation of the flash distillation bottoms. The additional distillation was performed as per above, but with a long path fractional distillation column (approximately 500 mm in length and a higher temperature of approximately 104° C. was used above the boiling point of the methoxyflurane). The first distillate fraction of approximately 50 ml was first collected and discarded, and the remaining distillate was collected over a 4 hour period, affording 245.10 g of about 99.9% pure methoxyflurane. The composition of that final distillate is shown in Table 1.

As used herein, the term “about”, when referring to a value or to an amount of mass, weight, time, volume, concentration, percentage, and the like can encompass variations of, and in some embodiments, ±20%, in some embodiments ±10%, in some embodiments ±5%, in some embodiments ±1%, in some embodiments ±0.5%, and in some embodiments ±0.1%, from the specified amount.

As used herein, the expression “room temperature” will be understood as encompassing a range of temperatures between about 20° C. and 25° C., with an average of about 23° C.

Throughout this specification and the claims which follow, unless the context requires otherwise, the word “comprise”, and variations such as “comprises” and “comprising”, will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The invention claimed is:

1. A process for purifying methoxyflurane from a reaction mixture derived from a batch synthetic procedure for producing the methoxyflurane, the process comprising the steps of:

a) adding one of an amine and an acid to the reaction mixture, b) adding a polar liquid to the mixture obtained in step a) to induce phase separation and formation of a polar phase and a separate organic phase, the organic phase containing the methoxyflurane, and c) adding the other one of the amine and the acid not used in step a) to the organic phase obtained in step b), to thereby purify the methoxyflurane.

2. The process of claim 1, further comprising a step d) of isolating the purified methoxyflurane.

3. The process of claim 1, wherein the methoxyflurane is produced using a precursor compound selected from (i) $Cl_2HC—CF_3$ and (ii) $Cl_2C{=}CF_2$.

4. The process of claim 1, the process being for purifying the methoxyflurane from impurities comprising one or more of methanol, 2,2-dichloro-1,1,1-trifluoroethane, methyl dichloroacetate, 1,1-dichloro-2,2-difluoroethylene, chloroform, and hydrogen fluoride.

5. The process of claim 1, the process being for purifying the methoxyflurane from impurities comprising one or more of methoxyethene (ME), orthoesters (OE), and methyl dichloroacetate (MDA).

6. The process of claim 5, wherein the orthoesters comprise 2,2-dichloro-1,1,1-trimethoxyethane.

7. The process of claim 1, wherein the amine is selected from ethylenediamine (1,2-diaminoethane), 1,3-diaminopropane, diethylenetriamine, di-n-propylamine, n-butylamine, ethanolamine, pyrrolidine, 2-aminobutane, and a combination thereof.

8. The process of claim 1, wherein the acid is selected from citric acid, hydrochloric acid, sulfuric acid, *sulphurous* acid, methanesulfonic acid, trifluoromethanesulfonic acid, phosphoric acid, acetic acid, trifluoroacetic acid, nitric acid, nitrous acid, hypochlorous acid, chlorous acid, chloric acid, perchloric acid, and a combination thereof.

9. The process of claim 1, wherein in step a) the amine or the acid is added according to a volume ratio from 0.25:1 to 2:1 relative to the reaction mixture.

10. The process of claim 1, wherein the acid is at least a 10% acid solution.

11. The process of claim 1, further comprising the steps of:

mixing a crude batch reaction mixture with a polar liquid to induce phase separation between a polar phase and a separate organic phase, and separating said organic phase from the polar phase, wherein the separated organic phase is the reaction mixture comprising the methoxyflurane.

12. The process of claim 1, further comprising the steps of:

separating the organic phase obtained in step b) from the polar phase, and adding a polar liquid to the mixture obtained in step c) to induce a phase separation between a polar phase and a separate organic phase, the organic phase comprising the methoxyflurane.

13. The process of claim 1, wherein the polar liquid is water.

14. The process of claim 1, wherein the purified methoxyflurane is isolated by distillation.

15. The process of claim 14, wherein the distillation comprises flash distillation to obtain a distillation bottoms liquid containing the methoxyflurane, followed by fractional distillation of said bottoms liquid.

16. The process of claim 1, wherein the methoxyflurane alkoxyethane has a purity of about 99.9%.

17. The process of claim 1, wherein the purified methoxyflurane has less than 1% methoxyethene (ME), orthoester (OE) and methyl dichloroacetate (MDA).

* * * * *